(12) United States Patent
Dreyfus et al.

(10) Patent No.: US 11,999,726 B2
(45) Date of Patent: Jun. 4, 2024

(54) 5-METHYL-4-FLUORO-THIAZOL-2-YL COMPOUNDS

(71) Applicant: Eli Lilly and Company, Indianapolis, IN (US)

(72) Inventors: Nicolas Jacques Francois Dreyfus, Surrey (GB); Peter James Lindsay-Scott, Northwood (GB)

(*) Notice: Subject to any disclaimer, the term of this patent is extended or adjusted under 35 U.S.C. 154(b) by 815 days.

(21) Appl. No.: 17/259,993

(22) PCT Filed: Jul. 24, 2019

(86) PCT No.: PCT/US2019/043219
§ 371 (c)(1),
(2) Date: Jan. 13, 2021

(87) PCT Pub. No.: WO2020/028115
PCT Pub. Date: Feb. 6, 2020

(65) Prior Publication Data
US 2021/0323958 A1 Oct. 21, 2021

Related U.S. Application Data

(60) Provisional application No. 62/712,266, filed on Jul. 31, 2018.

(51) Int. Cl.
*C07D 417/14* (2006.01)
(52) U.S. Cl.
CPC .................. *C07D 417/14* (2013.01)
(58) Field of Classification Search
CPC .................................................. C07D 417/14
See application file for complete search history.

(56) References Cited

U.S. PATENT DOCUMENTS

| | | | |
|---|---|---|---|
| 4,921,887 A | 5/1990 | Matsuo et al. |
| 9,120,781 B2 | 9/2015 | Li et al. |
| 10,081,625 B2 | 9/2018 | Dreyfus et al. |
| 10,377,750 B2 | 8/2019 | Dreyfus et al. |
| 2016/0031871 A1 | 2/2016 | Yu et al. |

FOREIGN PATENT DOCUMENTS

| | | |
|---|---|---|
| WO | 2005/014579 A1 | 2/2005 |
| WO | 2014/159234 A1 | 10/2014 |
| WO | 2016/030443 A1 | 3/2016 |
| WO | 2017/106254 A1 | 6/2017 |
| WO | 2017/144639 A1 | 8/2017 |
| WO | 2018/109198 A1 | 6/2018 |
| WO | 2018/109202 A1 | 6/2018 |

*Primary Examiner* — Golam M Shameem
(74) *Attorney, Agent, or Firm* — Robert D. Shereda

(57) ABSTRACT

The present invention provides a compound of Formula I: or a pharmaceutically acceptable salt thereof, and the use of compounds of Formula I for treating neurodegenerative diseases, such as Alzheimers disease.

(I)

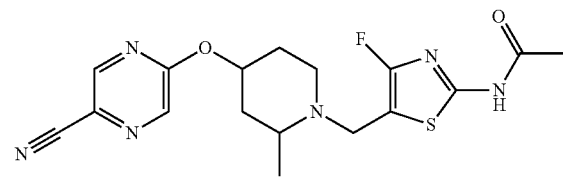

11 Claims, No Drawings

5-METHYL-4-FLUORO-THIAZOL-2-YL COMPOUNDS

The present invention relates to novel 5-methyl-4-fluoro-thiazol-2-yl compounds, to pharmaceutical compositions comprising the compounds, to methods of using the compounds to treat neurodegenerative disorders such as Alzheimer's disease (AD), and to intermediates and processes useful in the synthesis of the compounds.

The present invention is in the field of treatment of AD, progressive supranuclear palsy (PSP), and other diseases and disorders involving tau-mediated neurodegeneration, known collectively as tauopathies.

AD is a devastating neurodegenerative disorder that affects millions of patients worldwide. In view of the currently approved agents on the market which afford only transient symptomatic benefits to the patient, there is a significant unmet need in the treatment of AD.

The oligomerization of the microtubule-associated protein tau into filamentous structures such as paired helical filaments (PHFs) and straight or twisted filaments, which give rise to neurofibrillary tangles (NFTs) and neuropil threads (NTs), is one of the defining pathological features of AD and other tauopathies. The number of NFTs in the brains of individuals with AD has been found to correlate closely with the severity of the disease, suggesting tau has a key role in neuronal dysfunction and neurodegeneration (Nelson et al., *J Neuropathol Exp Neurol.*, 71(5), 362-381(2012)). Tau pathology has been shown to correlate with disease duration in PSP in that cases with a more aggressive disease course have a higher tau burden than cases with a slower progression. (Williams et al., *Brain,* 130, 1566-76 (2007)).

Past studies (Yuzwa et al., *Nat Chem Biol,* 4(8), 483-490 (2008)) support the therapeutic potential of O-GlcNAcase (OGA) inhibitors to limit tau hyperphosphorylation, and aggregation into pathological tau, for the treatment of AD and related tau-mediated neurodegeneration disorders. More recently, the OGA inhibitor Thiamet-G has been linked to slowing motor neuron loss in the JNPL3 tau mouse model (Yuzwa et al., *Nat Chem Biol,* 8, 393-399 (2012)), and to a reduction in tau pathology and dystrophic neurites in the Tg4510 tau mouse model (Graham et al., *Neuropharmacology,* 79, 307-313 (2014)). Accordingly, OGA inhibitors are recognized as a viable therapeutic approach to reduce the accumulation of hyperphosphorylated, pathological forms of tau.

WO 2018/109198 A1 and WO 2018/109202 A1 disclose certain OGA inhibitors useful for treating tauopathies, such as AD and PSP. In addition, US 2016/0031871 discloses certain glycosidase inhibitors for treating Alzheimer's disease.

OGA inhibitors that are brain penetrant are desired to provide treatments for tau-mediated neurodegeneration disorders, such as AD and PSP. The present invention provides certain novel compounds that are potent inhibitors of OGA. In addition, the present invention provides certain novel compounds that are potent inhibitors of OGA with the potential to be sufficiently brain penetrant to effectively treat tauopathies, such as AD and PSP.

Accordingly, the present invention provides a compound of Formula I:

Formula I

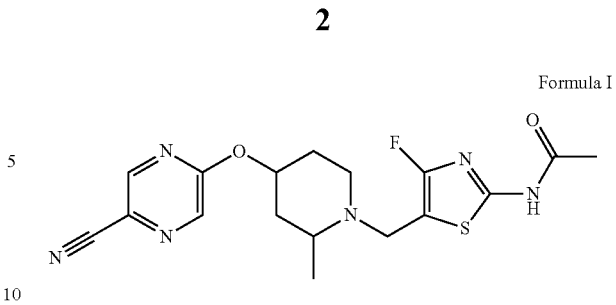

or a pharmaceutically acceptable salt thereof.

The present invention also provides a method of treating Alzheimer's disease in a patient in need of such treatment, comprising administering to the patient an effective amount of a compound of Formula I, or a pharmaceutically acceptable salt thereof.

The present invention further provides a method of preventing the progression of mild cognitive impairment to Alzheimer's disease in a patient in need of such treatment, comprising administering to the patient an effective amount of a compound of Formula I, or a pharmaceutically acceptable salt thereof.

The present invention also provides a method of treating progressive supranuclear palsy in a patient in need of such treatment, comprising administering to the patient an effective amount of a compound of Formula I, or a pharmaceutically acceptable salt thereof. The present invention also provides a method of treating tau-mediated neurodegenerative disorders in a patient, comprising administering to a patient in need of such treatment an effective amount of a compound of Formula I, or a pharmaceutically acceptable salt thereof.

Furthermore, this invention provides a compound of Formula I, or a pharmaceutically acceptable salt thereof for use in therapy, in particular for use in treating Alzheimer's disease or for use in preventing the progression of mild cognitive impairment to Alzheimer's disease. In addition, this invention provides a compound of Formula I, or a pharmaceutically acceptable salt thereof for use in treating progressive supranuclear palsy. The invention also provides a compound of Formula I, or a pharmaceutically acceptable salt thereof for use in treating tau-mediated neurodegenerative disorders.

Even furthermore, this invention provides the use of a compound of Formula I, or a pharmaceutically acceptable salt thereof, for the manufacture of a medicament for treating Alzheimer's disease or for preventing the progression of mild cognitive impairment to Alzheimer's disease. In addition, this invention provides the use of a compound of Formula I, or a pharmaceutically acceptable salt thereof, for the manufacture of a medicament for treating progressive supranuclear palsy. The invention also provides the use of a compound of Formula I, or a pharmaceutically acceptable salt thereof, for the manufacture of a medicament for treating tau-mediated neurodegenerative disorders.

The invention further provides a pharmaceutical composition, comprising a compound of Formula I, or a pharmaceutically acceptable salt thereof, with one or more pharmaceutically acceptable carriers, diluents, or excipients. The invention further provides a process for preparing a pharmaceutical composition, comprising admixing a compound of Formula I, or a pharmaceutically acceptable salt thereof, with one or more pharmaceutically acceptable carriers, diluents, or excipients.

Mild cognitive impairment has been defined as a potential prodromal phase of dementia associated with Alzheimer's disease based on clinical presentation and on progression of patients exhibiting mild cognitive impairment to Alzheimer's disease over time. The term "preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of the present invention are effective at a dosage per day that falls within the range of about 0.1 to about 15 mg/kg of body weight.

The compounds of the present invention are formulated as pharmaceutical compositions administered by any route which makes the compound bioavailable. Preferably, such compositions are for oral administration. Such pharmaceutical compositions and processes for preparing same are well known in the art (See, e.g., Remington: The Science and Practice of Pharmacy, L. V. Allen, Editor, 22$^{nd}$ Edition, Pharmaceutical Press, 2012).

The compounds of Formula I and the pharmaceutically acceptable salts thereof are particularly useful in the treatment methods of the invention, with certain configurations being preferred. The following list of compounds of the present invention describe such configurations. It will be understood that these preferences are applicable both to the treatment methods and to the compounds of the invention.

Compounds of the present invention include:

Formula Ia

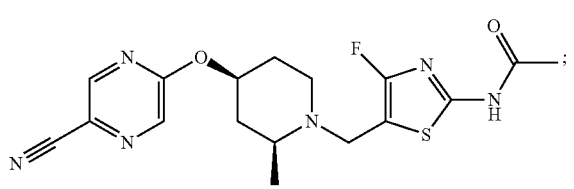

Formula Ib

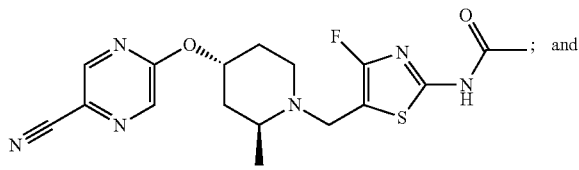

Formula Ic

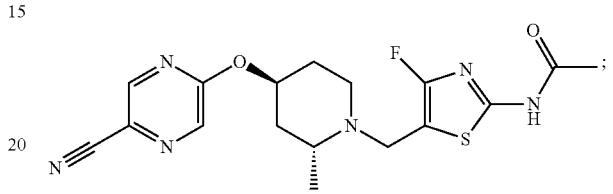

and

Formula Id

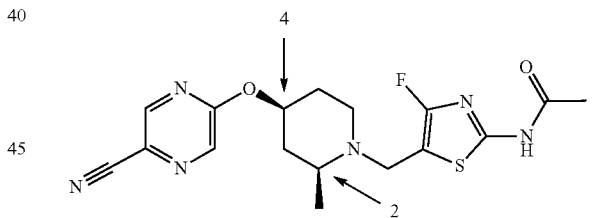

and pharmaceutically acceptable salts thereof.

The compound of Formula I wherein the methyl and oxygen substituents on the piperidine ring are in the cis or trans configuration, or pharmaceutically acceptable salt thereof, are included within the scope of the invention, with the cis configuration being preferred. For example, one of ordinary skill in the art will appreciate that the methyl at position 2 on the piperidine ring is in the cis configuration relative to the oxygen at position 4 as shown in Scheme A below:

Scheme A

Formula Ia

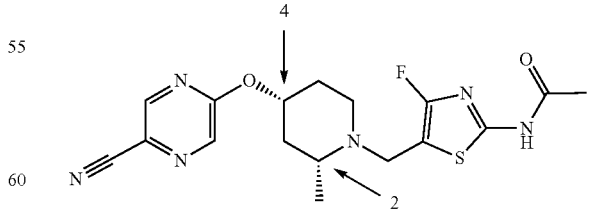

In addition, one of ordinary skill in the art will appreciate that the methyl at position 2 on the piperidine ring is in the trans configuration relative to the oxygen at position 4 as shown in Scheme B below:

Scheme B

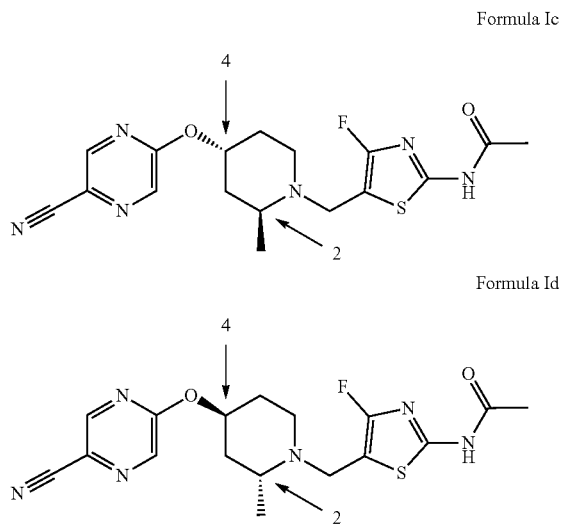

Formula Ic

Formula Id

Although the present invention contemplates all individual enantiomers and diasteromers, as well as mixtures of the enantiomers of said compounds, including racemates, the compound of Formula Ia and pharmaceutically acceptable salts thereof is particularly preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer,*" Agilent Technologies, July 2015).

A pharmaceutically acceptable salt of the compounds of the invention can be formed, for example, by reaction of an appropriate free base of a compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that compounds of Formula I may be prepared by using starting material or intermediate with the corresponding desired stereochemical configuration which can be prepared by one of skill in the art.

Certain abbreviations are defined as follows: "ACN" refers to acetonitrile; "Ac" refers to acetyl; "AcOH" refers to acetic acid; "Ac$_2$O" refers to acetic anhydride; "BOC" refers to tert-butoxycarbonyl; "CAS #" refers to Chemical Abstracts Registry number; "DCM" refers to methylene chloride or dichloromethane; "DIPEA" refers to diisopropylethylamine; "DMEA" refers to dimethylethylamine; "DMF" refers to N,N-dimethylformamide; "DMSO" refers to dimethyl sulfoxide; "EDTA" refers to ethylenediaminetetraacetic acid; "ES/MS" refers to Electrospray Mass Spectrometry; "EtOAc" refers to ethyl acetate; "EtOH" refers to ethanol or ethyl alcohol; "h" refers to hour or hours; "IPA" refers to isopropanol or isopropyl alcohol; "IPAm" refers to isopropyl amine; "LiHMDS" refers to lithium bis(trimethylsilyl)amide; "KOtBu" refers to potassium-tert-butoxide; "Me" refers to methyl; "MTBE" refers to methyl-tert-butyl ether; "min" refers to minute or minutes; "NaOtBu" refers to sodium-tert-butoxide; "n-BuLi" refers to n-butyllithium; "OAc" refers to acetate or acetoxy; "RT" refers to room temperature; "SCX" refers to selective cation exchange; "SFC" refers to Supercritical Fluid Chromatography; "TEA" refers to triethylamine; "TFA" refers to trifluoroacetic acid; "THF" refers to tetrahydrofuran; "TMA" refers to trimethylamine; "TMEDA" refers to tetramethylethylenediamine; "Tris" refers to tris(hydroxymethyl)aminomethane or 2-amino-2-(hydroxymethyl)propane-1,3-diol; "[α]$_D^{20}$" refers to specific optical rotation at 20° C. and 589 nm, wherein c is the concentration in g/mL.

Scheme 1

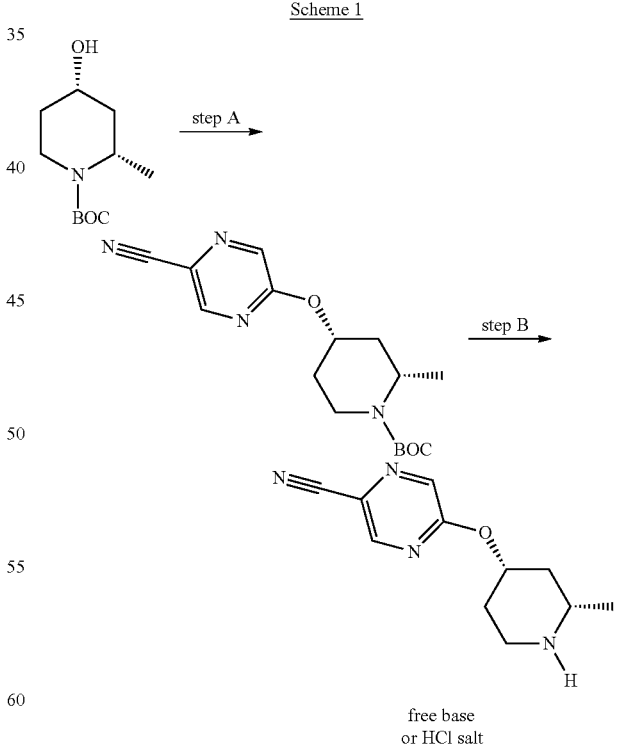

free base
or HCl salt

Scheme 1 depicts the synthesis 5-[[(2S,4S)-2-methyl-4-piperidyl]oxy]pyrazine-2-carbonitrile. Nucleophilic aromatic substitution is well known in the literature. As such, in Scheme 1, step A, about 1 equivalent of tert-butyl (2S,4S)-

4-hydroxy-2-methyl-piperidine-1-carboxylate (CAS #790667-99-1) and about 1.5 equivalents of 5-chloropyrazine-2-carbonitrile (CAS #36070-75-4) dissolved in an appropriate organic solvent, such as THF or 1,4-dioxane, may be treated with about 2 equivalents of a suitable base, such as NaH, NaOtBu, or KOtBu, at about 0° C. for about 60 min. The resulting reaction mixture may be warmed to RT with stirring for about 3-12 h. The resulting reaction product may be isolated by techniques well known in the art, such as extraction, precipitation, and filtration. For example, the reaction mixture may be diluted with saturated aqueous ammonium chloride and an appropriate organic solvent, such as DCM, MTBE, or EtOAc, the layers may be separated, and the organic extract may be washed with saturated NaCl, dried over Na$_2$SO$_4$, filtered, and the filtrate may be concentrated under reduced pressure. The resulting residue may be combined in about 10% MTBE/heptane, heated to about 45° C. for about 30 min, and cooled to RT with stirring. The resulting solids may be collected by filtration to obtain tert-butyl (2S,4S)-4-(5-cyanopyrazin-2-yl)oxy-2-methyl-piperidine-1-carboxylate, the product of Scheme 1, step A. Alternatively, the crude product after extraction may be isolated by flash chromatography on silica gel using an appropriate mixture of organic solvents, for example 1:0 to 0:1 iso-hexane:EtOAc, to afford the product of Scheme 1, step A, after evaporation of the chromatographic fractions.

Removal of the BOC protecting group is well described in the art. As such, about 1 equivalent of tert-butyl (2S,4S)-4-(5-cyanopyrazin-2-yl)oxy-2-methyl-piperidine-1-carboxylate, the product of Scheme 1, step A, may be dissolved in a suitable organic solvent, such as DCM, and treated with an excess of an acid solution, such as HCl in an alcoholic solvent, such as MeOH, EtOH, or iPrOH, HCl in a polar aprotic solvent, such as 1,4-dioxane, or TFA, neat or in a polar organic solvent, for about 0.1-8 h at about 0° C. to RT. The reaction product may be isolated by techniques well known in the art, such as extraction, precipitation, and filtration. For example, the reaction mixture may be partitioned between a mixture of an appropriate organic solvent, such as DCM, 2-methyltetrahydrofuran, MTBE, or a mixture thereof, and water, the layers may be separated, and the aqueous extracts may be neutralized with an appropriate aqueous base, such as NaOH, KOH, or Na$_2$CO$_3$. The basic aqueous mixture may be extracted with a suitable organic solvent such as DCM, the layers may be separated, and the organic extracts may be concentrated under reduced pressure. The resulting residue may be heated in a mixture of about 10% cyclopentyl methyl ether/heptane, heated to about 45° C. for about 30 min, and stirred at RT for about 30 min. The resulting solids may be collected by filtration to obtain 5-[[(2S,4S)-2-methyl-4-piperidyl]oxy]pyrazine-2-carbonitrile, the product of Scheme 1, step B. Additionally, the skilled artisan will recognize that the corresponding HCl salt may be obtained via treatment of tert-butyl (2S,4S)-4-(5-cyanopyrazin-2-yl)oxy-2-methyl-piperidine-1-carboxylate, the product of Scheme 1, step A, with HCl in an organic solvent as described above, with subsequent evaporation of the solvents under reduced pressure, to obtain the HCl salt of 5-[[(2S,4S)-2-methyl-4-piperidyl]oxy]pyrazine-2-carbonitrile.

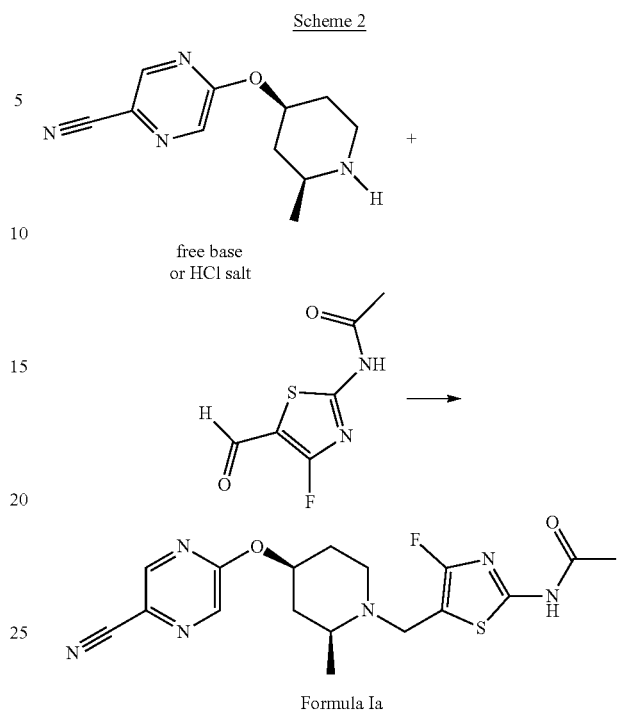

Scheme 2

Scheme 2 illustrates the preparation of the compound of Formula 1a. As is well appreciated in the art, reductive amination between a substituted amine and an aromatic aldehyde may be accomplished under a variety of conditions. For example, about 1 equivalent of N-(4-fluoro-5-formyl-thiazol-2-yl)acetamide and about 1 equivalent 5-[[(2S,4S)-2-methyl-4-piperidyl]oxy]pyrazine-2-carbonitrile (or the corresponding HCl salt) dissolved in a suitable organic solvent, such as EtOAc, EtOH or DCM, additionally containing about 3 equivalents of a suitable non-nucleophilic organic amine, such as DIPEA or pyridine, may be treated with about 3 equivalents of a suitable borohydride, such as Na(OAc)$_3$BH, for about 1.5 h to 18 h at about RT to 30° C. The reaction product may be isolated by techniques well known in the art, such as filtration, extraction, chromatography and precipitation/filtration. For example, the reaction mixture may be quenched with saturated aqueous Na$_2$CO$_3$, extracted with a suitable polar organic solvent, such as EtOAc, the organic layer may be separated, and the organic extract may be concentrated under reduced pressure. The resulting residue may be subjected to normal phase flash chromatography on silica gel, eluting with about 1:0 to 95:5 iPrOH/DCM or, alternatively, about 1:0 to 1:1 hexanes: EtOAc containing about 10% MeOH, to obtain a residue, after solvent evaporation. The residue may be dissolved in about 1:1 EtOH/heptane, heated to about 50° C. for about 30 min, and stirred at RT for about 10-30 min. The resulting solid may be collected by filtration to obtain N-[5-[[(2S,4S)-4-(5-cyanopyrazin-2-yl)oxy-2-methyl-1-piperidyl]methyl]-4-fluoro-thiazol-2-yl]acetamide, Formula Ia.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 μm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 μm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparation 1 tert-butyl (2S,4S)-4-(5-cyanopyrazin-2-yl)oxy-2-methyl-piperidine-1-carboxylate

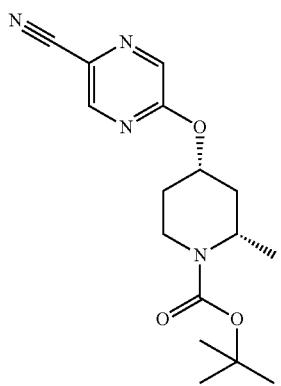 [SMILES: C[C@H]1C[C@@H](Oc2cnc(C#N)cn2)CCN1C(=O)OC(C)(C)C]

Scheme 1, step A: To a solution of tert-butyl (2S,4S)-4-hydroxy-2-methyl-piperidine-1-carboxylate (350 mg, 1.6 mmol) and THF (10 mL) at 0° C. is added KOtBu (274 mg, 2.4 mmol) in one portion and the mixture stirred for 45 min. 5-Chloropyrazine-2-carbonitrile (340 mg, 2.4 mmol) is added and the mixture is slowly allowed to warm to RT over 45 min with additional stirring at RT for 12 h. The reaction mixture is diluted with water (50 mL) and extracted with EtOAc (3×50 mL). The combined organic extracts are dried over MgSO$_4$, filtered, and concentrated under reduced pressure to afford crude oil. The resulting residue is dissolved in DCM and purified via flash chromatography over silica gel, eluting with a gradient of 1:0 to 0:1 iso-Hexane:EtOAc, to give the title compound (205 mg, 40% yield) after solvent evaporation of the pooled chromatographic fractions. ES/MS (m/z): 263 (M+H−C$_4$H$_9$).

Alternative Procedure for Preparation 1

To a flask is added tert-butyl (2S,4S)-4-hydroxy-2-methyl-piperidine-1-carboxylate (40.1 g, 186 mmol), 5-chloropyrazine-2-carbonitrile (39.0 g, 279 mmol) and THF (401 mL) at RT. The reaction mixture is stirred in a NaCl/ice-water bath (internal temperature −5° C.) and to the mixture is added NaOtBu (36.9 g, 372 mmol) portion wise over 10 min, maintaining an internal temperature below 10° C. during the addition. The reaction mixture is stirred in a NaCl/ice-water bath for 1 h (internal temperature −5° C.) and saturated aqueous NH$_4$Cl solution (300 mL) and water (100 mL) are added over 5 min. The mixture is transferred to a separating funnel, and extracted with MTBE (2×400 mL). The combined organic extracts are dried over Na$_2$SO$_4$ and concentrated under reduced pressure to give a residue, which is combined with 10% MTBE/heptane (350 mL). The resulting mixture is stirred vigorously in a 45° C. heating block for 30 min, stirred at room temperature for 30 min, and is filtered. The filtered solid is dried under vacuum at 40° C. to give the title compound as a pale brown solid (60 g, >99% yield). ES/MS (m/z): 341 (M+Na).

Preparation 2a

5-[[(2S,4S)-2-methyl-4-piperidyl]oxy]pyrazine-2-carbonitrile hydrochloride

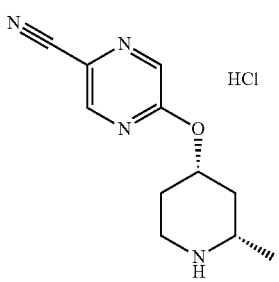 [SMILES: C[C@H]1C[C@@H](Oc2cnc(C#N)cn2)CCN1 ; Cl]

Scheme 1, step B: To a solution of tert-butyl (2S,4S)-4-(5-cyanopyrazin-2-yl)oxy-2-methyl-piperidine-1-carboxylate (205 mg, 0.6 mmol) is added a 4 M solution of HCl in 1,4-dioxane (5 mL, 20 mmol). The resulting mixture is stirred at RT for 3.5 h. The resulting suspension is concentrated under reduced pressure and placed under vacuum for 6 h to give the title compound (225 mg, >95% yield), suitable for use without additional purification. ES/MS (m/z): 219 (M+H).

Preparation 2b

5-[[(2S,4S)-2-methyl-4-piperidyl]oxy]pyrazine-2-carbonitrile

Scheme 1, step B: To a flask is added tert-butyl (2S,4S)-4-(5-cyanopyrazin-2-yl)oxy-2-methyl-piperidine-1-carboxylate (60 g, 188 mmol) and DCM (240 mL) at RT. The slurry is stirred in an ice-water bath (internal temperature 5° C.) and TFA (240 mL, 3174 mmol) is added dropwise over 15 min with gas evolution, maintaining an internal temperature below 10° C. during the addition. The reaction mixture is stirred in an ice-water bath for 10 min (internal temperature 5° C.) and is concentrated under reduced pressure. The resulting residue is stirred in an ice-water bath and combined with MTBE (200 mL) and water (200 mL). The mixture is transferred to a separating funnel and the layers are separated. The organic layer is extracted with 1% aqueous TFA solution (2×100 mL), further extracted with 0.1 M aqueous HCl solution (2×100 mL), and the organic layer is set aside.

The combined aqueous layers are stirred in an ice-water bath and 50% aqueous NaOH solution (42.8 mL, 754 mmol) is added over 5 min, maintaining an internal temperature below 20° C. during the addition. The resulting basified mixture is extracted with DCM (3×300 mL), and the combined organic extracts are dried over $Na_2SO_4$ and concentrated under reduced pressure to give the first batch of crude material. The organic layer from the first part of the workup is further extracted with 2 M aqueous HCl solution (2×100 mL). The combined aqueous layers are stirred in an ice-water bath and 50% aqueous NaOH solution (24.4 mL, 430 mmol) is added over 5 min, maintaining an internal temperature below 20° C. during the addition. The resulting basified mixture is extracted with DCM (3×100 mL) and the combined organic extracts are dried over $Na_2SO_4$ and concentrated under reduced pressure to give the second batch of crude material. The two batches of crude material are combined with 10% cyclopentyl methyl ether/heptane (181 mL) and the mixture is stirred vigorously in a 45° C. heating block for 30 min, cooled to RT and stirred for 30 min, and the resulting precipitate is collected by filtration. The filtered solid is dried under vacuum at 40° C. for 1 h to give the title compound as a cream-colored solid (29.2 g, 71% yield). ES/MS (m/z): 219 (M+H).

Alternative Procedure for Preparation 2b

To a flask is added tert-butyl (2S,4S)-4-(5-cyanopyrazin-2-yl)oxy-2-methyl-piperidine-1-carboxylate (1.2 g, 3.6 mmol). The flask is submerged in an ice-water bath and a solution of 5 M HCl in iPrOH (7.2 mL, 36.2 mmol) is added over 2 min. The reaction mixture is stirred at RT for 1.5 h and is concentrated under reduced pressure. The resulting residue is partitioned between DCM (10 mL) and saturated aqueous $NaHCO_3$ (10 mL) and the layers are separated. The aqueous layer is extracted with DCM (2×10 mL) and 2-methyltetrahydrofuran (4×10 mL). The combined organic extracts are dried over $Na_2SO_4$, filtered, and concentrated under reduced pressure. The resulting residue (804 mg, 3.7 mmol) is combined with another lot of similar purity (76 mg, 0.3 mmol). The mixed lot is combined with 10% cyclopentyl methyl ether/heptane (4.4 mL) and the mixture is stirred vigorously in a 45° C. heating block for 20 min, warmed to RT and stirred for 5 minutes, and the resulting precipitate is collected by filtration. The filtered solid is dried under vacuum at 40° C. for 1 h to give the title compound as a pale brown solid (649 mg, 74% yield from the two combined lots). ES/MS (m/z): 219 (M+H).

Preparation 3 tert-butyl
N-(4-fluoro-5-formyl-thiazol-2-yl)carbamate

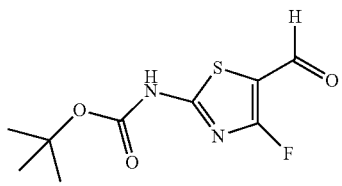 [SMILES: CC(C)(C)OC(=O)Nc1nc(F)c(C=O)s1]

CsF (227 g, 1480 mmol) is added to a solution of tert-butyl N-(4-chloro-5-formyl-thiazol-2-yl)carbamate (38.8 g, 148 mmol; see for example, N. Masuda, et al., *Bioorg Med Chem,* 12, 6171-6182 (2004)) in DMSO (776 mL) at RT. The reaction mixture is stirred in a 145° C. heating block with an internal temperature of 133° C. for 48 h, and the mixture is cooled in an ice-water bath. To the mixture is added saturated aqueous sodium bicarbonate solution (500 mL), saturated aqueous NaCl (500 mL) and EtOAc (500 mL). The mixture is stirred at RT for 10 min and is filtered through diatomaceous earth, washing with EtOAc (500 mL). The filtrate is transferred to a separating funnel and the layers are separated, the aqueous layer is extracted with EtOAc (1 L), the combined organic extracts are washed with saturated aqueous NaCl (1 L), and the aqueous layer is extracted with EtOAc (300 mL). The combined organic extracts are dried over $Na_2SO_4$, filtered, and concentrated under reduced pressure to give a residue. The residue is passed through a pad of silica gel (330 g), eluting with 5% EtOAc in DCM (1.5 L), and the filtrate is concentrated to give a residue. The resulting residue is dissolved in IPA (303 mL), filtered, and purified by SFC, using an IC column (cellulose polysaccharide derivative: tris (3,5-dichlorophenylcarbamate, 30×250 mm, 5μ), eluting with 10% IPA at 180 mL/min, 3 mL injections. The product-containing fractions are concentrated under reduced pressure to give the title compound (16.1 g, 49% yield). ES/MS (m/z): 247 (M+H).

Preparation 4

N-(4-fluoro-5-formyl-thiazol-2-yl)acetamide

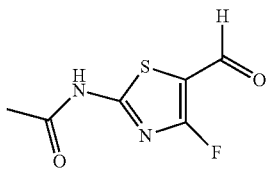

In a jacketed vessel, $ZnBr_2$ (91.9 g, 408 mmol) is added in one portion to a mixture of tert-butyl N-(4-fluoro-5-formyl-thiazol-2-yl)carbamate (33.5 g, 136 mmol) and DCM (503 mL) at RT. The reaction mixture is stirred overnight at an internal temperature of 37° C., the jacket temperature is set to −10° C., and THF (111 mL) is added dropwise over 15 min, maintaining an internal temperature below 6° C. The jacket temperature is then set to −30° C. and pyridine (110 mL, 1360 mmol) is added dropwise over 5 min, maintaining an internal temperature below 5° C. The jacket temperature is set to 0° C. and $Ac_2O$ (116 mL, 1220 mmol) is added dropwise over 5 min. The reaction mixture is stirred overnight at an internal temperature of 37° C., cooled to RT, and passed through a short pad of diatomaceous earth, eluting with THF (500 mL). The filtrate is transferred to a flask and the mixture is concentrated under reduced pressure to give a residue, which is concentrated from toluene (50 mL). To the resulting residue is added a solution of citric acid monohydrate (57.2 g, 272 mmol) in water (400 mL) and 2-methyltetrahydrofuran (400 mL), the mixture is stirred at 40° C. for 5 min, and passed through a short pad of diatomaceous earth, eluting with 2-methyltetrahydrofuran (100 mL). The filtrate is transferred to a separating funnel and the layers are separated. The aqueous layer is extracted with 2-methyltetrahydrofuran (2×250 mL) and the combined organic extracts are diluted with water (500 mL). To the mixture is added solid $NaHCO_3$ portion wise over 5 min with stirring, until gas evolution ceases. The mixture is transferred to a separating funnel, the layers are separated, and the aqueous layer is extracted with 2-methyltetrahydrofuran (200 mL and 100 mL). The combined organic extracts are dried over Na$_2$SO$_4$, filtered, and concentrated under reduced pressure to give a residue. The resulting residue is dissolved in 2-methyltetrahydrofuran (100 mL) and the mixture is passed through a short pad of silica gel (250 g), eluting with 2-methyltetrahydrofuran (2.5 L). The filtrate is concentrated under reduced pressure to give a residue which is suspended in a 1:1 mixture of DCM and heptane (202 mL). The mixture is stirred at room temperature for 30 min, the resulting solid is collected by filtration, and the filtered solid is dried under vacuum at 40° C. for 2 h, to obtain the title compound (18 g, 70% yield). ES/MS (m/z): 189.0 (M+H).

Alternative Procedure for Preparation 4

Under an inert atmosphere, dissolve tetramethylammonium fluoride tetrahydrate (100 kg, 605 mol) in IPA (453-459 kg) and concentrate under reduced pressure to volume ~150-180 L at temperatures <70° C. Add IPA (453-459 kg) and concentrate under reduced pressure to 150-180 L. Repeat until mixture has a KF<0.2%. Add DMF (546-552 kg), heat to 90° C., and concentrate under reduced pressure to ~150 L. Add back DMF (453-459 kg) and concentrate under reduced pressure to 150 L. Repeat until mixture has a residual IPA limit of <60 ppm. Add N-(4-chloro-5-formylthiazol-2-yl)acetamide (15 kg, 73.3 mol) and DMF (149 kg), and heat to 100° C. for 2-4 h. Adjust the temperature to 20-25° C. and add 2-methyltetrahydrofuran (248 kg). Add 25% weight aqueous NH$_4$Cl (458 kg) and stir for 30 min. Separate the layers and wash the aqueous layer with additional 2-methyltetrahydrofuran (248 kg). Separate the resulting layers, wash the combined organic extract with 25% weight aqueous NH$_4$Cl (2×458 kg), and stir for 30 min. Add EtOAc (180 kg) and heat the reaction mixture to reflux for 1 h to obtain a clear solution. Concentrate the mixture under reduced pressure at <55° C. to a volume of about 30 L. Add EtOAc (54 kg) and concentrate the mixture under reduced pressure at <55° C. to a volume of about 30 L. Stir the mixture at 20-25° C. for 2 h under nitrogen. Collect the resulting solids by filtration and dry under vacuum at 55-65° C. for 10-12 h to obtain the title compound (4.5 kg, 82.5% purity).

Example 1

N-[5-[[(2S,4S)-4-(5-cyanopyrazin-2-yl)oxy-2-methyl-1-piperidyl]methyl]-4-fluoro-thiazol-2-yl]acetamide

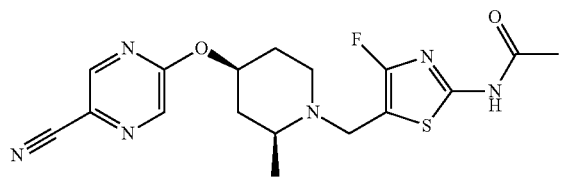 [SMILES: CC(=O)Nc1nc(F)c(CN2CC[C@H](Oc3cnc(C#N)cn3)C[C@@H]2C)s1]

Scheme 2: To a solution of N-(4-fluoro-5-formyl-thiazol-2-yl)acetamide (166 mg, 0.9 mmol) and 5-[[(2S,4S)-2-methyl-4-piperidyl]oxy]pyrazine-2-carbonitrile hydrochloride (225 mg, 0.9 mmol) in DCM (10 mL) is added DIPEA (0.46 mL, 2.6 mmol). The resulting solution is stirred at RT for 1.75 h. To the solution is added NaBH(OAc)$_3$ (561 mg, 2.6 mmol). The resulting solution is stirred at RT for 16 h. The reaction is slowly quenched with saturated aqueous NaHCO$_3$ (5 mL) and the aqueous layer is extracted with DCM (2×10 mL). The combined organic extracts are dried over MgSO$_4$, filtered, and the filtrate is concentrated under reduced pressure. The resulting residue is dissolved in DCM and purified via flash chromatography over silica gel, eluting with a gradient of 1:0 to 1:1 hexanes:EtOAc followed by elution with 1:1 to 0:1 hexanes:EtOAc containing 10% MeOH, to obtain the title compound (52 mg, 15% yield). ES/MS (m/z): 391 (M+H). [α]$_D^{20}$=+38° (c=1.0, MeOH).

Alternative Procedure for Example 1

To a flask is added 5-[[(2S,4S)-2-methyl-4-piperidyl]oxy]pyrazine-2-carbonitrile (35.6 g, 163 mmol), EtOAc (768 mL), pyridine (26.4 mL, 326 mmol) and NaBH(OAc)$_3$ (104 g, 490.7 mmol) at RT. The reaction mixture is stirred in a 31° C. heating block (internal temperature 30° C.) and N-(4-fluoro-5-formyl-thiazol-2-yl)acetamide (30.7 g, 163 mmol) is added portion wise over 2 min. The reaction mixture is stirred in a 31° C. heating block overnight (internal temperature 30° C.) and is cooled in an ice-water bath with stirring. To the resulting mixture is added a saturated aqueous solution of NaHCO$_3$ (500 mL) over 5 min, while maintaining the internal temperature below 10° C. during the addition. The resulting mixture is stirred at RT for 15 min, partitioned between water (100 mL) and EtOAc (50 mL), and the mixture is transferred to a separating funnel. The resulting layers are separated. The aqueous layer is extracted with 2-methyltetrahydrofuran (2×300 mL). The combined organic extracts are dried over Na$_2$SO$_4$, filtered, and concentrated under reduced pressure. The resulting residue is combined with a solution of saturated aqueous NaHCO$_3$ (300 mL) and the mixture is extracted with DCM (3×300 mL), leaving the brown rag layer in the aqueous phase. The combined organic extracts are dried over Na$_2$SO$_4$, filtered, and concentrated under reduced pressure. The resulting residue is purified by flash chromatography over silica, eluting with a gradient of 0-5% iPrOH/DCM, and the product-containing fractions are combined and concentrated under reduced pressure. The resulting residue is concentrated from heptane (2×50 mL). The resulting solid is combined with 50% EtOH/heptane (318 mL), the mixture is stirred vigorously in a 50° C. heating block for 30 min, and cooled to room temperature with stirring for 10 min. The resulting precipitate is collected by filtration and the filter cake is washed with heptane (25 mL). The collected solid is dried under vacuum at RT for 5 min and dried under vacuum at 40° C. overnight to obtain the title compound, N-[5-[[(2S,4S)-4-(5-cyanopyrazin-2-yl)oxy-2-methyl-1-piperidyl]methyl]-4-fluoro-thiazol-2-yl]acetamide, as a pale cream-colored crystalline solid (47 g, 72% yield). ES/MS (m/z): 391 (M+H). [α]$_D^{20}$=+47.2° (c=0.25, MeOH).

X-Ray Powder Diffraction

The XRD patterns of crystalline solids are obtained on a Bruker D4 Endeavor X-ray powder diffractometer, equipped with a CuKα source (λ=1.54060 Å) and a Vantec detector, operating at 35 kV and 50 mA. The sample is scanned between 4 and 40° in 2θ (2-theta), with a step size of 0.0087° in 2θ and a scan rate of 0.5 sec/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35—National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of degrees 2θ), typically the more prominent peaks. The crystal form diffraction patterns, collected at ambient temperature and relative humidity, are adjusted based on NIST 675 standard peaks at 8.85 and 26.77 degrees 2-θ.

Thus, a crystalline sample of Example 1 is characterized by an XRD pattern using CuKα radiation as having diffraction peaks (2θ values) as described in Table 1 below. Specifically the pattern contains a peak at 12.1° in combination with one or more of the peaks selected from the group consisting of 18.5°, 13.0°, and 16.0°, with a tolerance for the diffraction angles of 0.2 degrees.

TABLE 1

X-ray powder diffraction peaks of the crystalline free base of Example 1.

| Peak | Angle (°2θ) +/− 0.2° | Relative Intensity (% of most intense peak) |
| --- | --- | --- |
| 1 | 8.1 | 75.2 |
| 2 | 10.1 | 39.2 |
| 3 | 12.1 | 100.0 |
| 4 | 13.0 | 78.0 |
| 5 | 13.7 | 53.3 |
| 6 | 16.0 | 77.9 |
| 7 | 18.5 | 95.0 |
| 8 | 20.6 | 67.4 |
| 9 | 22.9 | 71.3 |
| 10 | 26.4 | 63.0 |

In Vitro Human OGA Enzyme Assay

Generation of OGA Enzyme

The nucleotide sequence encoding full-length human O-GlcNAc-β-N-acetylglucosaminidase (NM_012215) is inserted into pFastBac1 (Invitrogen) vector with an N-terminal poly-histidine (HIS) tag. Baculovirus generation is carried out according to the Bac-to-Bac Baculovirus Expression system (Invitrogen) protocol. Sf9 cells are infected at 1.5×10$^6$ cells/mL using 10 mL of P1 virus per Liter of culture and incubated at 28° C. for 48 hrs. Cells are spun down, rinsed with PBS and the pellets stored at −80° C. The above OGA protein (His-OGA) is purified as follows: 4 L of cells are lysed in 200 mL of buffer containing 50 mM Tris, pH 8.0, 300 mM NaCl, 10% glycerol, 10 mM imidazole, 1 mM dithiothreitol (DTT), 0.1% Triton™ X-100, 4 tablets of protease inhibitors (complete EDTA-Free, Roche) for 45 min at 4° C. This cell lysate is then spun for 40 min at 16500 rpm at 4° C., and supernatant incubated with 6 mL of Ni-NTA resin (nickel-nitrilotriacetic acid) for 2 hours at 4° C.

Resin is then packed onto column and washed with 50 mM Tris, pH 8.0, 300 mM NaCl, 10% glycerol, 10 mM imidazole, 0.1% Triton™ X-100, 1 mM DTT, followed by 50 mM Tris, pH 8.0, 150 mM NaCl, 10 mM imidazole, 10% glycerol, 1 mM DTT. The proteins are eluted with 50 mM Tris, pH 8.0, 150 mM NaCl, 300 mM imidazole, 10% glycerol, 1 mM DTT. Pooled His-OGA containing fractions are concentrated to 6 ml and loaded onto Superdex75 (16/60). The protein is eluted with 50 mM Tris, pH 8.0, 150 mM NaCl, 10% glycerol, 2 mM DTT. Fractions containing His-OGA are pooled and protein concentration measured with BCA (Bradford Colorimetric Assay).

OGA Enzyme Assay

The OGA enzyme catalyses the removal of O-GlcNAc from nucleocytoplasmic proteins. To measure this activity Fluorescein di-N-acetyl-β-N-acetyl-D-glucosaminide (FD-GlcNAc, Kim, Eun Ju; Kang, Dae Ook; Love, Dona C.; Hanover, John A. Carbohydrate Research (2006), 341(8), 971-982) is used as a substrate at a final concentration of 6.7 μM. This fluorogenic substrate becomes fluorescent upon cleavage by OGA, so that the enzyme activity can be measured by the increase in fluorescence detected at 535 nm (excitation at 485 nm).

The assay buffer is prepared to give a final concentration of 50 mM H$_2$NaPO$_3$—HNa$_2$PO$_3$, 0.01% bovine serum albumin and 0.01% Triton™ X-100 in water, at pH 7. Compounds to be tested are diluted in pure dimethyl sulfoxide (DMSO) using ten point concentration response curves. Maximal compound concentration in the reaction mixture is 30 or 1 μM. Compounds at the appropriate concentration are pre-incubated with OGA enzyme for 30 minutes before the reaction is started by the addition of substrate. The final enzyme concentration is 3.24 nM or 0.5 nM, for the 30 or 1 μM maximal compound concentration, respectively. Reactions are allowed to proceed for 60 min at room temperature. Then, without stopping the reaction, fluorescence is read. IC$_{50}$ values are calculated by plotting the normalized data vs. log of the compound and fitting the data using a four parameter logistic equation.

The compound of Example 1 was tested essentially as described above and exhibited an IC$_{50}$ of 0.343+0.141 nM (n=3). These results demonstrate that the compound of Example 1 inhibits OGA enzyme activity in vitro.

We claim:

1. A compound of the formula;

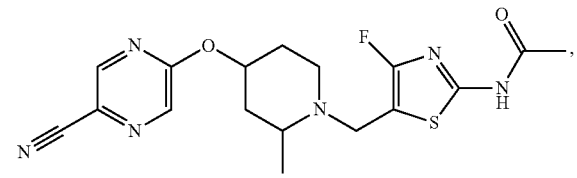 [SMILES: CC(=O)Nc1nc(F)c(CN2CCC(Oc3cnc(C#N)cn3)CC2C)s1]

or a pharmaceutically acceptable salt thereof.

2. The compound according to claim 1 wherein the methyl at position 2 on the piperidine ring is in the cis configuration relative to the oxygen at position 4:

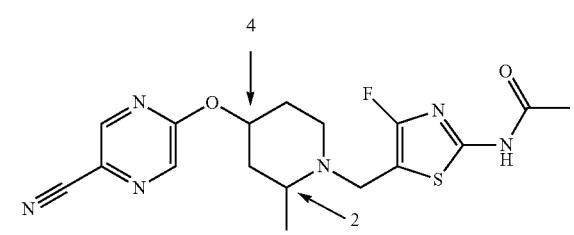 [SMILES: CC(=O)Nc1nc(F)c(CN2CCC(Oc3cnc(C#N)cn3)CC2C)s1]

or a pharmaceutically acceptable salt thereof.

3. The compound according to claim 1 wherein the compound is:

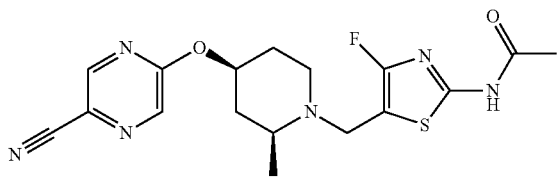 [SMILES: CC(=O)Nc1nc(F)c(CN2CC[C@H](Oc3cnc(C#N)cn3)C[C@@H]2C)s1]

or a pharmaceutically acceptable salt thereof.

4. The compound according to claim 3 wherein the compound is:

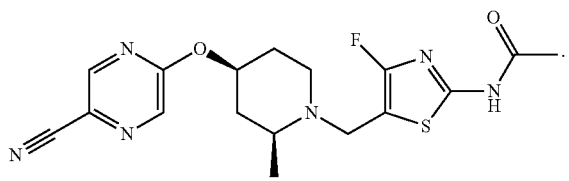 [SMILES: CC(=O)Nc1nc(F)c(CN2CC[C@H](Oc3cnc(C#N)cn3)C[C@@H]2C)s1]

5. The compound according to claim 4 which is crystalline.

6. The compound according to claim 5 which is characterized by a peak in the X-ray diffraction spectrum, at diffraction angle 2-theta of 12.1° in combination with one or more of the peaks selected from the group consisting of 18.5°, 13.0°, and 16.0°, with a tolerance for the diffraction angles of 0.2 degrees.

7. A method of treating Alzheimer's disease in a patient, comprising administering to a patient in need of such treatment an effective amount of a compound of claim 1, or a pharmaceutically acceptable salt thereof.

8. A method of treating the progression of mild cognitive impairment to Alzheimer's disease in a patient, comprising administering to a patient in need of such treatment an effective amount of a compound of claim 1, or a pharmaceutically acceptable salt thereof.

9. A method of treating progressive supranuclear palsy in a patient, comprising administering to a patient in need of such treatment an effective amount of a compound of claim 1, or a pharmaceutically acceptable salt thereof.

10. A pharmaceutical composition, comprising a compound or a pharmaceutically acceptable salt thereof according to claim 1, with one or more pharmaceutically acceptable carriers, diluents, or excipients.

11. A process for preparing a pharmaceutical composition, comprising admixing a compound or a pharmaceutically acceptable salt thereof according to claim 1 with one or more pharmaceutically acceptable carriers, diluents, or excipients.

* * * * *